US006635745B2

(12) United States Patent
Sedrani et al.

(10) Patent No.: US 6,635,745 B2
(45) Date of Patent: Oct. 21, 2003

(54) RAPAMYCIN ASSAY

(75) Inventors: Richard Sedrani, Basel (CH); Valérie Quesniaux Ryffel, Allschwil (CH)

(73) Assignee: Novartis AG, Basel (CH)

( * ) Notice: Subject to any disclaimer, the term of this patent is extended or adjusted under 35 U.S.C. 154(b) by 19 days.

(21) Appl. No.: 09/757,212

(22) Filed: Jan. 9, 2001

(65) Prior Publication Data

US 2002/0022717 A1 Feb. 21, 2002

Related U.S. Application Data

(63) Continuation of application No. 09/072,278, filed on May 4, 1998, now abandoned, which is a continuation of application No. 08/532,837, filed as application No. PCT/EP94/01006 on Mar. 30, 1994, now abandoned.

(30) Foreign Application Priority Data

Apr. 8, 1993 (GB) .............................................. 9307491

(51) Int. Cl.$^7$ .......................... C07K 1/10; C07K 16/44; G01N 33/535
(52) U.S. Cl. ................... 530/405; 435/7.93; 435/7.94; 435/7.95; 530/403; 530/404; 530/388.9
(58) Field of Search ................................ 530/403, 405, 530/404, 388.9; 436/815

(56) References Cited

U.S. PATENT DOCUMENTS

| | | | |
|---|---|---|---|
| 4,650,803 A | | 3/1987 | Stella et al. |
| 5,100,883 A | | 3/1992 | Schiehser |
| 5,118,677 A | | 6/1992 | Caufield |
| 5,118,678 A | | 6/1992 | Kao et al. |
| 5,130,307 A | | 7/1992 | Failli et al. |
| 5,151,413 A | | 9/1992 | Caufield et al. |
| 5,169,773 A | * | 12/1992 | Rosenthaler et al. |
| 5,177,203 A | | 1/1993 | Failli et al. |
| 5,194,447 A | | 3/1993 | Kao |
| 5,258,389 A | | 11/1993 | Goulet et al. |
| 5,322,772 A | | 6/1994 | Soldin |
| 5,504,091 A | | 4/1996 | Molnar-Kimber et al. |
| 5,532,137 A | * | 7/1996 | Niwa et al. |
| 5,665,772 A | | 9/1997 | Cottens et al. |
| 5,750,413 A | * | 5/1998 | Morrison et al. |
| 6,187,547 B1 | * | 2/2001 | Legay et al. |

FOREIGN PATENT DOCUMENTS

| | | |
|---|---|---|
| EP | 0 293 892 | 2/1988 |
| EP | 0 450 936 | 10/1991 |
| EP | 0 524 832 | 1/1993 |
| EP | 693 132 B1 | 12/1997 |
| WO | 8 602 080 | 4/1986 |
| WO | WO-92/05179 * | 4/1992 |
| WO | WO 94/25022 | 11/1994 |
| WO | WO 94/25072 | 11/1994 |
| WO | WO 94/25468 | 11/1994 |

OTHER PUBLICATIONS

B. Erlanger, Methods in Enzymology, vol. 70, pp. 85–104, Academic Press, Inc. (1990).*
D. Yelton et al, American Scientist, vol. 68, 510–516 (1980).*
E. Sevier et al, Clinical Chemistry, vol. 27(11), 1797–1806 (1981).*
Campbell, Monoclonal Antibody and Immunosensor Technology, Chapter 1, Elsevier, NY (1991).*
Database WPI, Section Ch, Week 9008, Derwent Publications Ltd., London, GB; AN 90–053405.
JP,A,2 000 495 (Tosoh Corp.) Jan. 5, 1990.
Yatscoff R.W. et al., Therapeutic Drug Monitoring, pp. 478–482 (1993).
Kahan B.D., et al., Clinical Transplantation, No. 14, pp. 97–109 (2000).
Jones et al., Clinical Therapeutics, vol. 22, Suppl. B, pp. B49–B61 (2000).

* cited by examiner

Primary Examiner—Mary E. Ceperley
(74) Attorney, Agent, or Firm—Gabriel Lopez; Diane E. Furman

(57) ABSTRACT

Monoclonal antibodies to rapamycin and to 40-O-alkylated derivatives of rapamycin are provided, together with novel haptens, immunogenic conjugates, and processes for making them and assay kits for using them.

4 Claims, 8 Drawing Sheets

Figure 1:
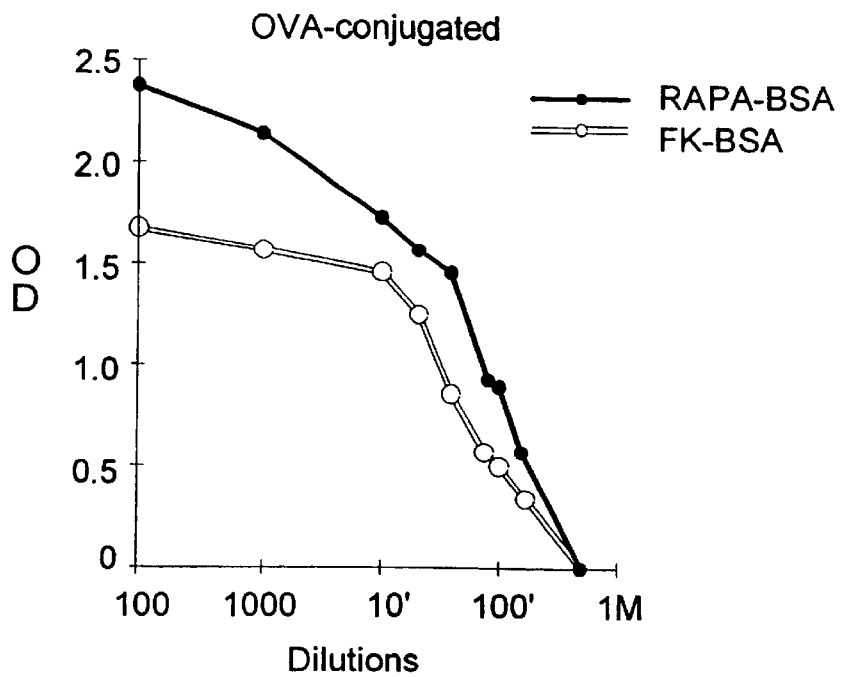
Figure 1:
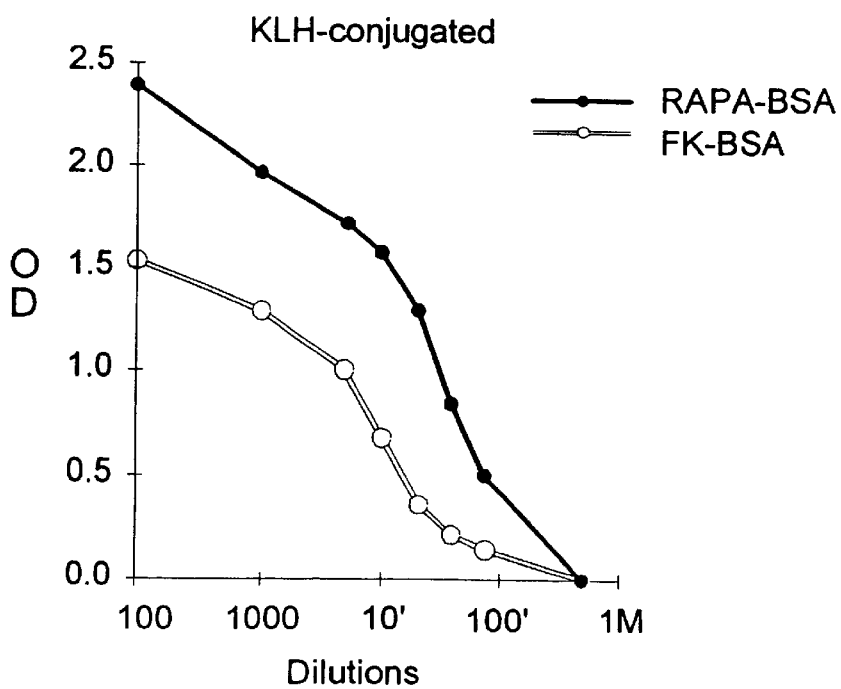

Specificity of mAbs to Rapamycin for Rapamycin (□) vs. FK 506 (△) in competitive ELISA.

A

B

C

RAPAMYCIN ASSAY

This is a continuation of application Ser. No. 09/072,278, May 4, 1998, abandoned, which is a continuation of application Ser. No. 08/532,837, Oct. 5, 1995, abandoned, which is a 371 of PCT/EP94/01006, Mar. 30, 1994.

This invention relates to monoclonal antibodies to rapamycin and rapamycin derivatives, which are useful, e.g., in assay kits for monitoring blood levels of drug.

Rapamycin is a macrolide antibiotic produced by *Streptomyces hygroscopicus*, which has been found to be pharmaceutically useful in a variety of applications, particularly as an immunosuppressant, e.g., for use in the treatment and prevention of organ transplant rejection and autoimmune diseases. Rapamycin, however, does exhibit side effects at higher dosages, and it has a somewhat variable bioavailability. Monitoring blood levels of rapamycin in patients being treated with rapamycin is thus very desirable in order to be able to regulate the dosage so as to maintain the minimum level sufficient for pharmacologic activity and to avoid any undue risk of side effects. The lack of a sensitive and reliable assay which can be performed quickly and easily in a clinical setting has been a major obstacle to the development of rapamycin as a pharmaceutical.

Previous efforts to develop assay kits for clinical monitoring of rapamycin have not been particularly successful. EP 041795, for example, describes a microbiological assay in which rapamycin concentration is measured as a function of antifungal activity. WO 92/02946 provides an assay system which measures rapamycin levels indirectly by measuring competition for binding to macrophilin. Both of these assays are cumbersome and not particularly sensitive. Even more importantly, both of these assays may have considerable variation under slightly different test conditions, making comparisons of test results from different hospitals difficult.

There have been no previous reports of monoclonal antibodies which recognize rapamycin. There are inherent difficulties in making monoclonal antibodies to rapamycin because rapamycin is not immunogenic and is itself extremely immunosuppressive. Moreover, as the metabolites of rapamycin have not been well characterized in the literature, it is difficult to identify a monoclonal antibody capable of differentiating between rapamycin and its metabolites.

The present invention provides monoclonal antibodies which are highly sensitive to rapamycin. The antibodies of the invention are produced in response to inoculation with a novel immunogenic conjugate comprising a novel derivative of rapamycin linked to an immunogenic protein. Assay kits using these antibodies are well suited for use in a clinical setting and provide far more accurate and reproducible results than was previously possible. The antibodies are also useful in the purification and isolation of rapamycin.

Providing assay systems for immunosuppressive derivatives of rapamycin present similar challenges. Of particular interest are 40-O-derivatives of rapamycin, i.e., rapamycins which are O-substituted at the hydroxy on the cyclohexyl ring (position 40), e.g., as described in U.S. Pat. No. 5,258,389 and PCT/EP 93/02604 (O-aryl and O-alkyl rapamycins) (both incorporated herein by reference); especially 40-O-alkylated rapamycins where the 40-O-substituent is alkyl or substituted alkyl; e.g., hydroxyalkyl, hydroxyalkoxyalkyl, acylaminoalkyl, or aminoalkyl, wherein "alk-" or "alkyl" refers to $C_{1-6}$ alkyl, branched or linear, preferably $C_{1-3}$ alkyl, in which the carbon chain may be optionally interrupted by an ether (—O—) linkage; most especially 40-O-(2-hydroxyethyl)-rapamycin, 40-O-(3-hydroxypropyl)-rapamycin, 40-O-[2-(2-hydroxy)ethoxy]ethyl-rapamycin, and 40-O-(2-acetaminoethyl)-rapamycin). Thus a further object of the invention is to provide monoclonal antibodies to such 40-O-derivatives. Such antibodies are useful in diagnostic assays and also in the purification and production of the derivatives.

The novel activated derivatives of rapamycin used to make the novel immunogenic conjugates of the invention are rapamycins which are linked through one of the hydroxy groups on the rapamycin, preferably the hydroxy group located on the cyclohexyl portion of the rapamycin (position 40) or the hydroxy at position 28, to an activated coupling group, i.e., a group capable of direct reaction with a protein to form a covalent linkage without the requirement for the use of a coupling agent (e.g., carbodiimide reagents) to enable, effect, or promote the reaction with the protein. Preferably, the activated coupling group has an activated ester or carboxy group, i.e., of formula —CO—O—X where X is a carboxy activating group such as o- or p-nitrophenyl, 1-benztriazole, pentafluorophenyl, or (especially) N-succinimido. Other suitable activated coupling groups are, for example, i) activated dithio groups, e.g., of formula —S—S—Z wherein Z is a dithio activating group such as 2-pyridyl, which may be linked to the rapamycin; or ii) epoxy groups, e.g., epoxy methyl. The activated coupling group may be linked to the rapamycin by means of an ester, ether, amide, thio or other suitable linkage, but ester linkage is preferred. Most preferably, the activated coupling group contains a bis-ester moiety, e.g., succinyl, having an ester linkage to the rapamycin at one end and the activated ester or activated carboxy group at the other.

The preferred rapamycin derivatives of the invention are those of formula III below which are produced according to Reaction I:

Reaction I
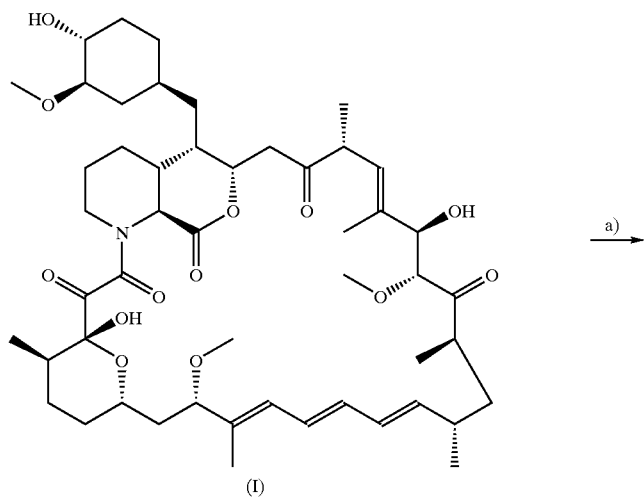
(I)
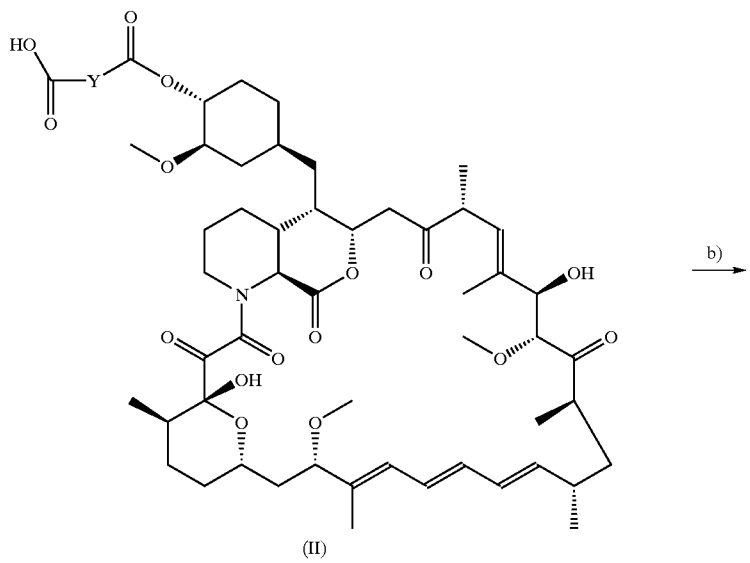
(II)
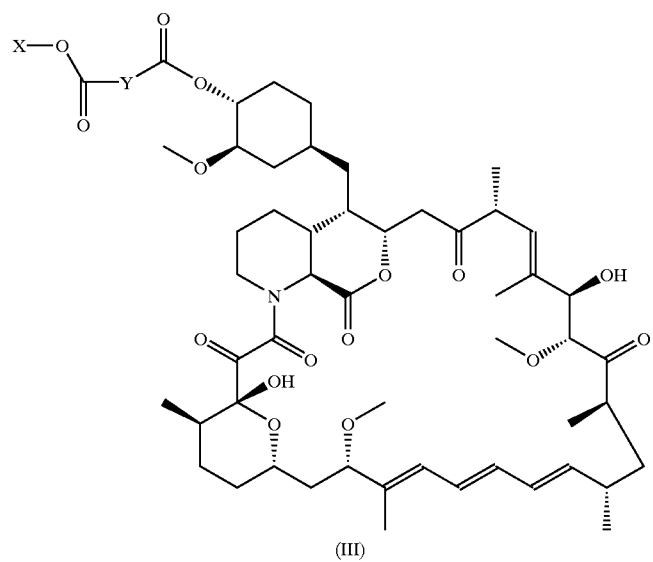
(III)

wherein formula I is rapamycin, which is a) reacted with an acylating agent, e.g., a cyclic anhydride or a dicarboxylic acid (optionally in hemi-O-protected form), under suitable conditions and deprotection if necessary to yield the rapamycin of formula II, wherein Y is a spacer moiety, preferably a lower alkylene, e.g., $C_{2-6}$ alkylene, most preferably ethylene. This rapamycin of formula II is then b) activated by reaction with a carboxy activating group, e.g. of formula HO—X where X is as defined above, to yield the activated rapamycin of formula III.

A preferred activated derivative of rapamycin is the succinimido derivative of formula III below, prepared, e.g., according to Reaction II:

Reaction II

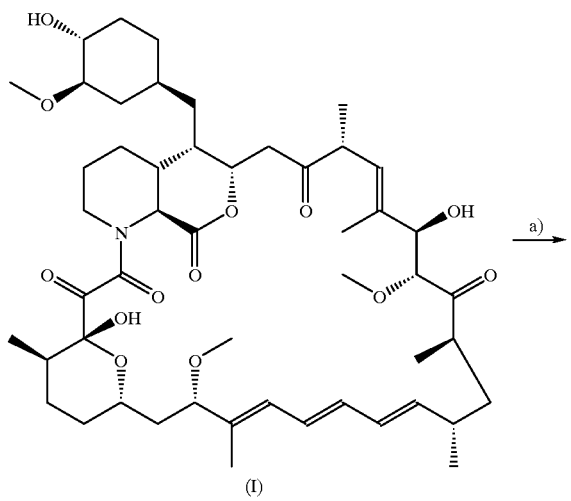

(I)

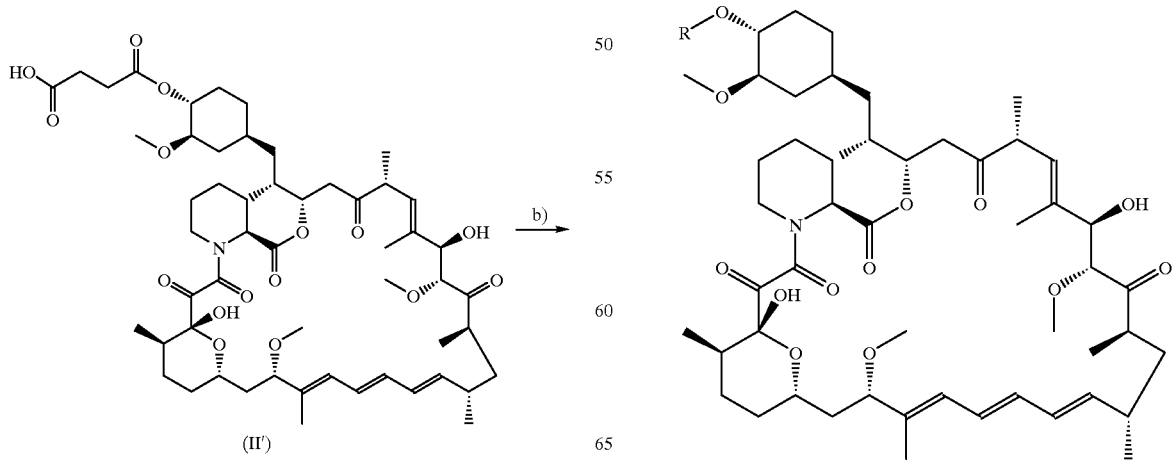

(II')

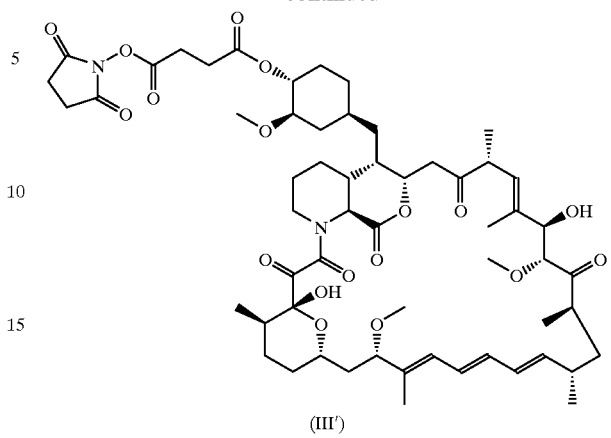

(III')

wherein formula I is rapamycin, which is a) 0-acylated using succinic anhydride in the presence of DMAP and pyridine to form the rapamycin hemisuccinate of formula II' (40-O-(3-Carboxy)propanoyl-rapamycin); which is then b) activated with N-Hydroxy succinimide in the presence of EDC, $Et_3N$, and $CH_2Cl_2$ to form the 40-O-succinimidooxysuccinyl rapamycin of formula III', e.g., as described more fully in example 1 below. Monoclonal antibodies produced using a hapten such as this which is linked through the 40-position will ordinarily be cross reactive between rapamycin and a 40-O-derivative of rapamycin, such as described above. Such monoclonal antibodies can be selected as described below for compounds which recognize a particular region of the rapamycin or 40-O-derivative of the rapamycin, e.g., in the binder domain or effector domain, as described below.

It is in some cases desirable to have monoclonal antibodies capable of fine sensitivity to modifications in the cyclohexyl region, e.g., for distinguishing between rapamycin and the 40-O rapamycin derivatives, or for identifying metabolites in the cyclohexyl region. In such a case, the hapten is preferably linked through the 28-O position rather then the 40-O position. For example, the rapamycin derivative of formula A:

Formula A wherein R is an O-protecting group, or a substituent as described above, e.g., hydroxyalkyl, hydroxyalkoxyalkyl, acylaminoalkyl, or aminoalkyl, optionally in protected form, is reacted according to Reaction I, deprotecting if necessary, to give the analogous 28-O activated hapten, for example a compound of formula B:

Formula B

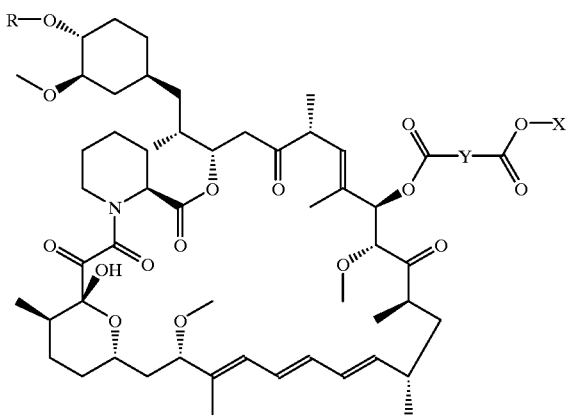

wherein R1 is H, or an O-substituent as described above, e.g., hydroxyalkyl, hydroxyalkoxyalkyl, acylaminoalkyl, or aminoalkyl, Y is a linker moiety as defined above, and X is a carboxy activating group as defined above. In preparing this hapten, where R is an O-protecting group or an O-protected substituent, the acylating agent may optionally be, e.g., a dicarboxylic acid in hemi-O-protected form, so that following acylation, both O-protecting groups may be removed in one step prior to adding the carboxy activating group. For example, haptens for generating monoclonal antibodies capable of recognizing 40-O-(2-hydroxyethyl)-rapamycin, can be produced by protecting the primary hydroxy, acylating the hydroxy at position 28 with a dicarboxylic acid in hemi-O-protected form, deprotecting, and activating the carboxy group, e.g., according to Reaction III:

Reaction III

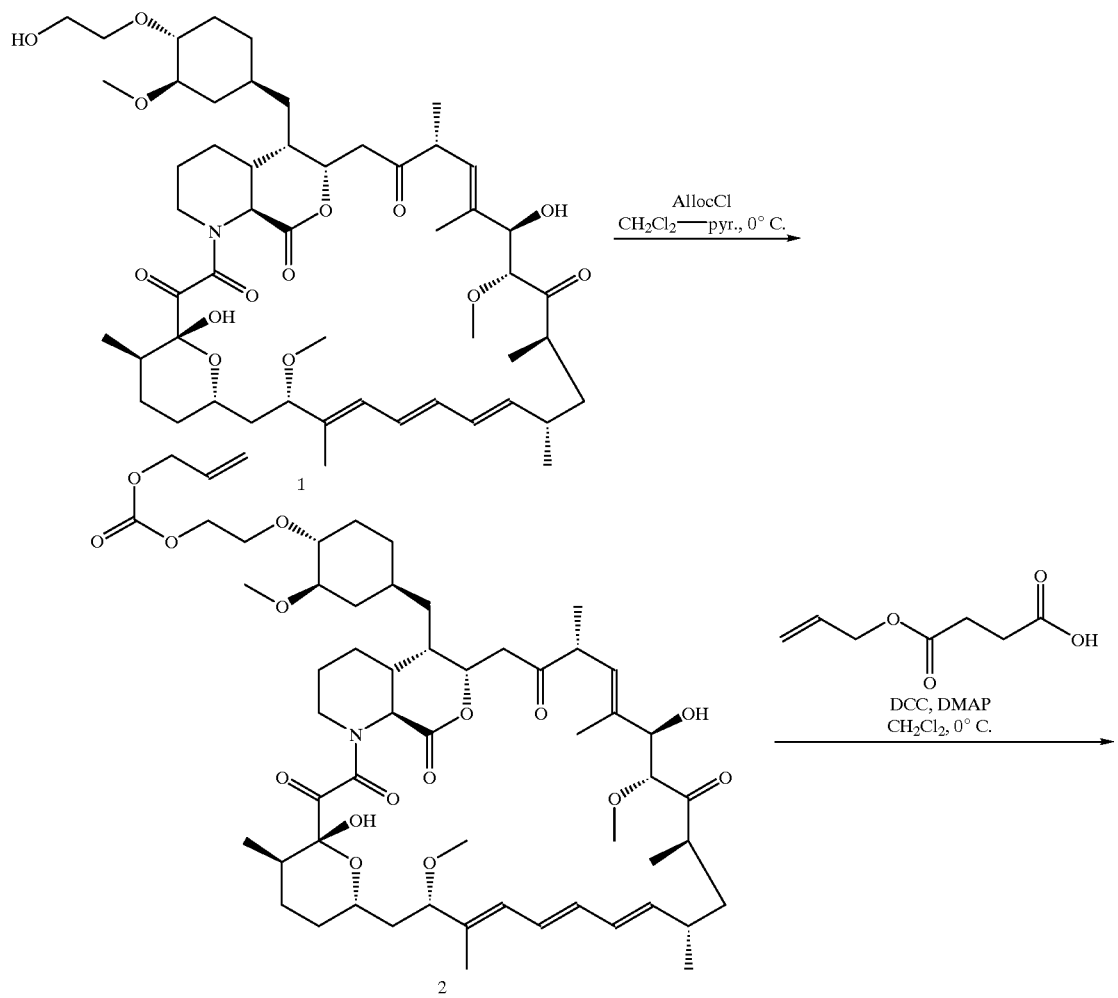

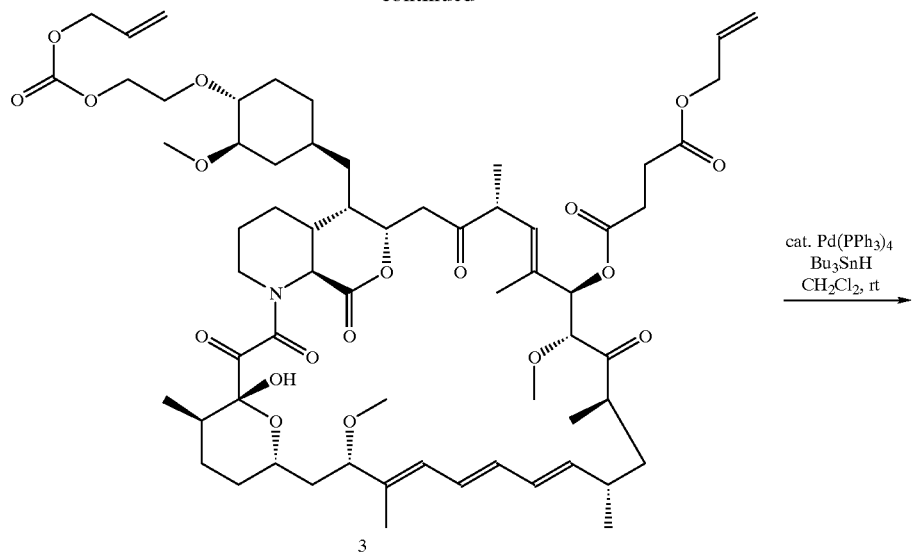
cat. Pd(PPh₃)₄
Bu₃SnH
CH₂Cl₂, rt
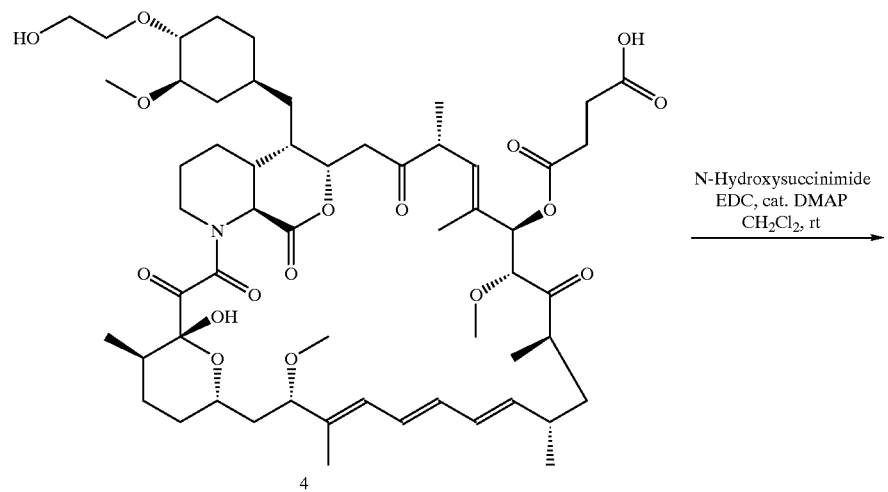
N-Hydroxysuccinimide
EDC, cat. DMAP
CH₂Cl₂, rt
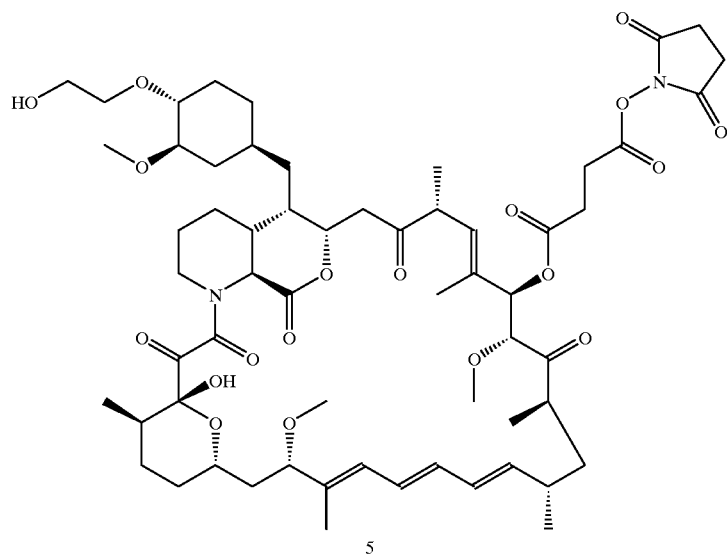

Similarly, rapamycin itself may be activated at the 28-O rather than the 40-O, by O-protecting the C40 hydroxy, acylating the hydroxy group in position 28 with a hemi-O-protected dicarboxylic acid, deprotecting, and activating the carboxy group, e.g., according reaction IV:
Reaction IV
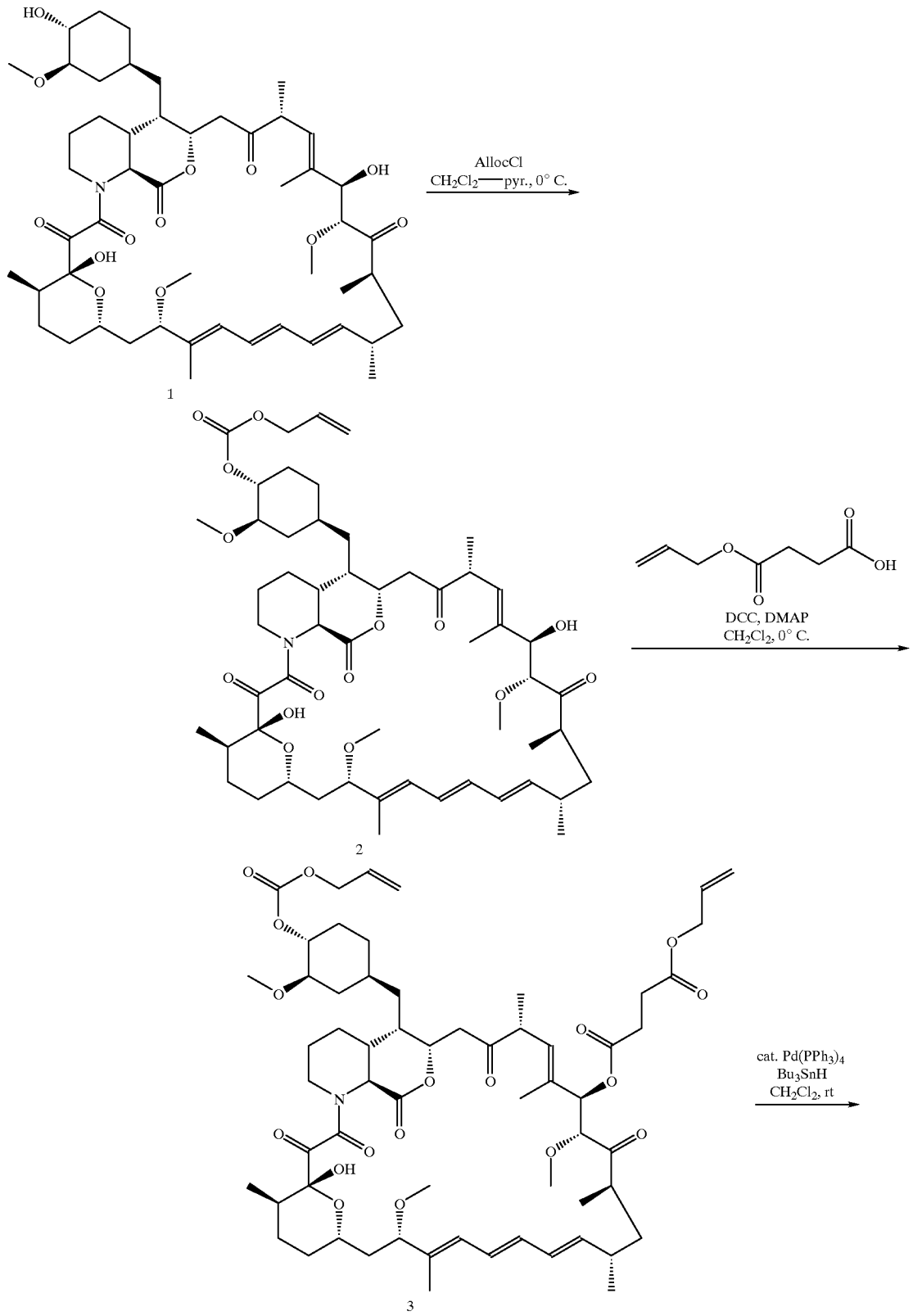

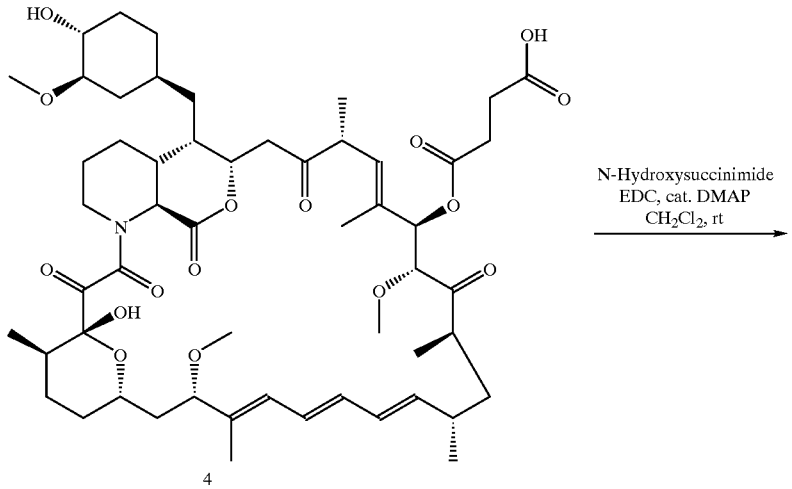

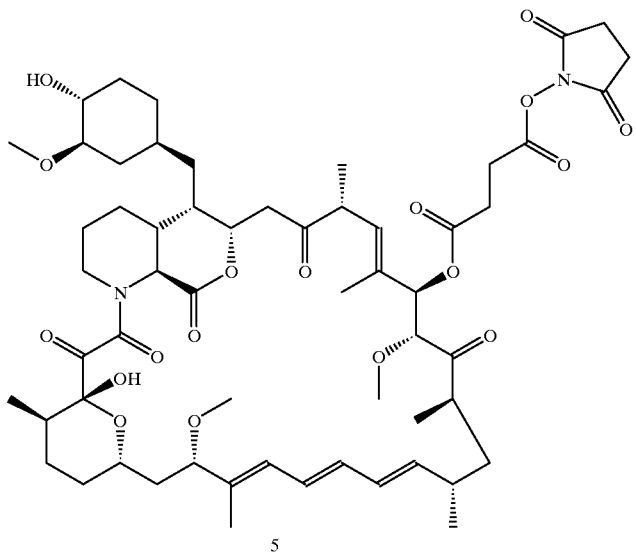

The activated rapamycin or rapamycin derivative is then linked to a suitable immunogenic protein, e.g., bovine serum albumin (BSA), ovalbumin (OVA), or keyhole limpet hemocyanine (KLH) to form an immunogenic conjugate. Monoclonal antibodies are prepared using conventional methods, e.g., administering the novel immunogenic conjugate to a suitable animal species to effect immunogenic challenge and recovering antibody-producing cells sensitized to said conjugate; immortalizing said antibody producing cells by fusion with a suitable myeloma; and recovering the monoclonal antibody from a selected immortalized cell line thus established.

The antibodies of the invention may then be used in a suitable assay. Several possibilities would be clear to one skilled in the art. One approach is a competitive assay using antibody and a rapamycin tracer, for example wherein microtiter plates are coated with antibody and exposed to a competitor which is a labeled (e.g., fluoro- or radio-labeled, especially biotinylated) rapamycin, in the presence and absence of test fluid believed to possibly contain a rapamycin, e.g., plasma or whole blood from the patient. The plates are rinsed, and the amount of labeled competitor which has bound to the antibody is measured, which amount varies inversely with the amount of rapamycin in the test fluid. Another approach is an ELISA using antibody, a rapamycin protein conjugate, and a labeled (e.g., enzyme-labeled) tracer antibody recognizing murine IgG, for example wherein microtiter plates are coated with a rapamycin-protein conjugate (e.g., the immunogenic conjugate described above comprising a protein linked to rapamycin or a 40-O-alkylated rapamycin), exposed to antibody in the presence and absence of test fluid, rinsed, and antibody binding to the rapamycin conjugate detected by binding of the tracer antibody to the antibody bound to the rapamycin conjugate. Again, the amount of bound antibody will vary inversely with the amount of rapamycin in the test sample. In either case, the assay is standardized with test solutions containing known concentrations of rapamycin. An assay kit comprising (i) the monoclonal antibody of the invention, preferably in lyophilized form or coated onto a microtiter plate, and (ii) optionally also comprising either a rapamycin protein conjugate, optionally coated onto a plate, and/or a labeled rapamycin derivative, and (iii) further optionally comprising a rapamycin solution for standardization and instructions for use, is therefore provided. Such a kit is capable of detecting rapamycin at concentrations of below 10 ng/ml, e.g., below 1 ng/ml, e.g., as low as 0.25–0.5 ng/ml.

The antibodies of the invention may be further characterized by their relative binding affinity to an immunosuppressive ascomycin, e.g., FK-506. FK-506 is an immunosuppressive macrolide having some structural similarity to rapamycin in the binding domain. Rapamycins (e.g., rapamycin and its immunosuppressant derivatives) and FK-506 both bind to macrophilins (FKBPs), and for both it is believed that macrophilin binding is a necessary but not a sufficient criteria for immunosuppressive activity. The effector region of rapamycin, however, is quite different from FK-506, and indeed, the two compounds have quite different mechanisms of activity. (FK-506 for example appears to cause immunosuppression primarily by suppressing IL-2 transcription, whereas rapamycin has no significant effect on IL-2 transcription.) Rapamycins can thus be characterized as having an FKBP binding domain and an effector domain, and a distinction can be made between rapamycin metabolites which are modified in the FKBP binding domain from those modified in the effector domain. This distinction can be made with the monoclonal antibodies of the invention by measuring the relative cross-reactivity of the monoclonal antibodies of the invention with FK-506 (cross-reactivity being measured, e.g., in a competitive ELISA): monoclonal antibodies having a high degree of cross reactivity (e.g., greater than 50%) recognize epitopes in the FKBP binding domain of rapamycin which is similar to FK-506; monoclonal antibodies with a low degree of cross reactivity (e.g., less than 20%, optimally less than 10%) recognize epitopes in the effector region, which is unique to rapamycins.

Antibodies of the invention can also be screened and characterized according to their ability to distinguish between rapamycin and a 40-O-derivative of rapamycin, e.g., as defined above. Where it is desired that the antibodies do not distinguish between rapamycin and a 40-O-derivative of rapamycin, antibodies are selected which show at least 70%, preferably greater than 90%, cross-reactivity between rapamycin and a 40-O-derivative thereof. In such a case, the hapten used to make the monoclonal antibody is preferably a 40-O-activated rapamycin, e.g., of formula III in Reaction I. Where it is desired to distinguish between rapamycin and a 40-O-derivative or metabolite of rapamycin, antibodies are selected having less than 30%, preferably less than 10%, cross-reactivity thereto. In this case, the hapten used to make the antibody is preferably a 28-O-activated rapamycin or rapamycin derivative, e.g., of formula B.

EXAMPLE 1

Production of 40-O-activated Rapamycin a) Production of 40-O-hemisuccinate of Rapamycin To a stirred solution of 1.5 g (1.64 mmol) of rapamycin and 0.577 g (5.77 mmol) of succinic anhydride in 12 mL of pyridine is added 195 mg (1.64 mmol) of DMAP. The resulting mixture is stirred at ambient temperature for 19 h and concentrated under reduced pressure. The residue is dissolved in ethyl acetate and washed three times with water. The organic solution is dried over anhydrous sodium sulfate, filtered and concentrated under reduced pressure. The residue is purified by column chromatography on silica gel using 9:1 $CH_2Cl_2$—MeOH. The fractions containing the expected product are combined and purified once more by column chromatography on silica gel using 19:1 $CH_2Cl_2$—MeOH to afford, after removal of the solvent under reduced pressure, 40-O-(3-carboxy)propanoyl-rapamycin (the rapamycin hemisuccinate of formula II' supra) as a white foam showing the following characteristic spectroscopic properties:

$^1$H NMR (CDCl$_3$) δ2.68 (7H, m, H33, H25 and O$_2$CC$\underline{H}_2$C$\underline{H}_2$CO$_2$H), 3.14 (3H, s and m, OCH$_3$ and H39), 3.34 (3H, s, OCH$_3$), 3.38 (3H, s, OCH$_3$), 4.68 (1H, m, H40), 4.72 (1H, broad s, 10-OH); MS (FAB) m/z 1036 ([M+Na]$^+$), 982 ([M-CH$_3$O]$^+$), 964 ([M-(CH$_3$O+H$_2$O)]$^+$), 946 ([M-(CH$_3$O+2H$_2$O)]$^+$).

b) Production of 40-O-succinimidooxysuccinyl-rapamycin

To a stirred solution of 120 mg (0.118 mmol) of the rapamycin hemisuccinate of step a), 16.5 μL (0.118 mmol) of Et$_3$N and 22.7 mg (0.118 mmol) of EDC in 8 mL of $CH_2Cl_2$ is added 13.6 mg (0.118 mmol) of N-hydroxysuccinimide. The resulting mixture is stirred for 18 h at room temperature, then diluted with ethyl acetate and washed twice with water. The organic solution is dried over anhydrous sodium sulfate, filtered and concentrated under reduced pressure. The residue is purified by column chromatography on silica gel (ethyl acetate) to afford 40-O-succinimidooxysuccinyl-rapamycin (i.e., the compound of formula III' in Reaction II supra) as a white foam having the following characteristic spectroscopic properties:

$^1$H NMR (DMSO) δ2.67 (2H, t, O$_2$CC$\underline{H}_2$CH$_2$CO$_2$), 2.81 (7H, s, CH$_3$O and succimide CH$_2$), 2.92 (2H, t, O$_2$CC$_2$C$\underline{H}_2$CO$_2$), 4.55 (1H, m, H40), 5.26 (1H, d, 28-OH), 6.43 (1H, s, 10-OH); MS (FAB) m/z 1133 ([M+Na]$^+$), 1111 ([M+H]$^+$), 1092 ([M-H$_2$O]$^+$), 1079 ([M-CH$_3$O]$^+$), 1061 ([M-(CH$_3$O+H$_2$O)]$^+$), 1043 ([M-(CH$_3$O+2H$_2$O)]$^+$).

EXAMPLE 2

Production of 28-O-activated 40-O Derivative of Rapamycin a) 28-O-hemisuccinate of 40-O-(2-hydroxyethyl)-rapamycin To a stirred, cooled (0° C.) solution of 958 mg (1.00 mmol) of 40-O-(2-hydroxyethyl)-rapamycin in 2.2 mL of 10:1 methylene chloride-pyridine is added 0.160 mL (1.50 mmol) of allyl chloroformate. Stirring is continued at 0° C. and two portions each of 0.080 mL (1.00 mmol) of pyridine and 0.053 mL (0.50 mmol) of allyl chloroformate are added after 3 hours and 4 hours respectively. After the last addition of reagents, stirring was continued for one more hour, and the reaction is quenched with 1M aqueous sodium bicarbonate. The resulting mixture is extracted three times with ethyl acetate. The organic solution is washed successively with 1N aqueous hydrochloric acid, 1N aqueous sodium bicarbonate and saturated brine, then dried over anhydrous sodium sulfate, filtered and concentrated under reduced pressure. The residue is purified by column chromatography on silica gel (50:50 hexane-ethyl acetate) to afford the allyloxycarbonyl protected compound (formula 2 in reaction III above) as a white foam.

To a stirred, cooled (0° C.) solution of 208 mg (0.200 mmol) of this product in 2 mL of methylene chloride is added 2.4 mg (0.020 mmol) of DMAP and 82 mg (0.400 mmol) of DCC, followed by a solution of 63 mg (0.400 mmol) of monoallylsuccinate in 0.5 mL of methylene chloride. The reaction mixture is stirred at 0° C. for 14 hours and the resulting suspension was filtered through a fritted glass funnel. The organic solution is concentrated under reduced pressure, and the residue is purified by column chromatography on silica gel (30:70 hexane-ethyl acetate) giving the product (formula 3 of reaction III above) as a white foam.

To a stirred solution of 177 mg (0.150 mmol) of this product in 5 mL of methylene chloride is added 17.3 mg (0.015 mmol) of tetrakis(triphenylphosphine)palladium and 0.080 mL (0.3 mmol) of tributyltin hydride. The yellow solution is stirred for 2 hours at ambient temperature and diluted with ethyl acetate, washed once with cold 2N aqueous citric acid and three times with saturated brine, dried over anhydrous sodium sulfate, filtered and concentrated under reduced pressure. Column chromatography on silica gel (85:15 ethyl acetate-methanol) affords the hemisuccinate (formula 4 of reaction III) as a pale yellow oil.

b) 28-O-succinimidooxysuccinyl-40-O-(2-hydroxyethyl)-rapamycin

A solution of 53 mg (0.050 mmol) of the hemisuccinate of step a) in 2.5 mL of methylene chloride is treated with 2 mg of DMAP, 24 mg (0.125 mmol) of EDC and 14 mg (0.125 mmol) of N-hydroxysuccinimide. After stirring for 2 hours at ambient temperature, the reaction is quenched with 1N aqueous sodium bicarbonate. The mixture is extracted with three portions of ethyl acetate. The organic solution is washed with aqueous sodium bicarbonate and brine, dried over anhydrous sodium sulfate, filtered and concentrated to give the title activated hapten (the compound of formula 5 of reaction III), which is used for the preparation of the protein-hapten conjugate without further purification, and which has the following characteristic spectrascopic properties:

$^1$H NMR (CDCl$_3$) δ2.43 (1H, dd, H33a), 2.50–2.98 (10H, m, H25, H33b, succinate hydrogens, succinimide hydrogens), 3.58 (2H, m, H6b, 1 hydroxyethyl H), 3.68 (3H, m, H16, 2 hydroxyethyl H), 3.81 (2H, m, H14, 1 hydroxyethyl H), 3.93 (1H, d, H27), 5.28 (2H, m, H2, H30), 5.34 (1H, d, H28); MS (FAB) 1161 ([M+Li]$^+$).

EXAMPLE 3

Production of 28-O-activated Rapamycin a) 28-O Hemisuccinate of Rapamycin

To a stirred, cooled (0° C.) solution of 914 mg (1.00 mmol) of rapamycin in 2.2 mL of 10:1 methylene chloride-pyridine is added 0.212 mL (2.00 mmol) of allyl chloroformate. After 3 hours 0.080 mL (1.000 mmol) of pyridine and 0.053 mL (0.50 mmol) of allyl chloroformate are added. Stirring is continued for one more hour, and the reaction is quenched with 1M aqueous sodium bicarbonate. The resulting mixture is extracted three times with methyl-t-butylether. The organic solution is washed successively with cold 1N aqueous hydrochloric acid, 1N aqueous sodium bicarbonate and saturated brine, then dried over anhydrous sodium sulfate, filtered and concentrated under reduced pressure. The residue is purified by column chromatography on silica gel (70:30 hexane-ethyl acetate) to afford the allyloxycarbonyl protected compound (formula 2 in reaction IV) as a white foam.

To a stirred, cooled (0° C.) solution of 400 mg (0.400 mmol) of this product in 5 mL of methylene chloride is added 4.8 mg (0.040 mmol) of DMAP and 164 mg (0.800 mmol) of DCC, followed by a solution of 127 mg (0.800 mmol) of monoallylsuccinate in 1 mL of methylene chloride. The reaction mixture is stirred at −15° C. for 14 hours and the resulting suspension is filtered through a fritted glass funnel. The organic solution is concentrated under reduced pressure and the residue is purified by column chromatography on silica gel (40:60 hexane-methyl-t-butylether) giving the compound of formula 3 of Reaction IV as a white foam.

To a stirred solution of 285 mg (0.250 mmol) of this product in 5 mL of methylene chloride is added 28.8 mg (0.025 mmol) of tetrakis(triphenylphosphine)palladium and 0.133 mL (0.5 mmol) of tributyltin hydride. The yellow solution is stirred for 1 hour at ambient temperature and diluted with methyl-t-butylether, washed twice with cold 2N aqueous citric acid and three times with saturated brine, dried over anhydrous sodium sulfate, filtered and concentrated under reduced pressure. Column chromatography on silica gel (90:10-60:40 methyl-t-butylether-methanol) affords the 28-O rapamycin hemisuccinate (the compound of formula 4, reaction IV) as a pale yellow oil.

b) 28-O-succinimidooxysuccinyl-rapamycin

A solution of 51 mg (0.050 mmol) of the product of step a) in 2 mL of methylene chloride is treated with 2 mg of DMAP, 24 mg (0.125 mmol) of EDC and 14 mg (0.125 mmol) of N-hydroxysuccinimide. After stirring for 4 hours at ambient temperature, the reaction is quenched with 1N aqueous sodium bicarbonate. The mixture is extracted with three portions of methyl-t-butylether. The organic solution is washed with aqueous sodium bicarbonate and brine, dried over anhydrous sodium sulfate, filtered and concentrated to give the activated title compound, which is used for the preparation of the protein-hapten conjugate without further purification and which exhibits the following characteristic spectrascopic properties:

$^1$H NMR (CDCl$_3$) δ2.43 (1H, dd, H33a), 2.55-3.02 (11H, m, H25, H33b, H39, succinate hydrogens, succinimide hydrogens), 3.56 (1H, m, H6b), 3.68 (1H, dd, H16), 3.83 (1H, m, H14), 3.93 (1H, d, H27), 5.28 (2H, m, H2, H30), 5.34 (1H, d, H28); MS (FAB) 1117 ([M+Li]$^+$).

EXAMPLE 4

Production of Immunogenic Conjugates a) 40-O-linked Rapamycin Conjugates 17.4 mg of the 40-O-activated rapamycin of example 1 is dissolved in 400 μl DMF or DMSO. 120 μl (i.e., containing 5.22 mg activated rapamycin) of this solution is added dropwise with vigorous stirring to a solution containing 8 mg of KLH in 2 ml 0.1 M NaHCO$_3$ buffer (pH 7.7). The reaction mixture is stirred for 2 hours at room temperature, and the resulting rapamycin-KLH conjugate is purified by dialysis at 4° C. against 5 l PBS, 3× over 48 hours. The conjugate is optionally further concentrated by centrifugation using microconcentrator tubes. Rapamycin-BSA and rapamycin-OVA conjugates are prepared in the same manner, substituting BSA or OVA respectively for KLH in the above procedure.

b) 28-O-linked (optionally 40-O-alkylated) Rapamycin Conjugates 5 mg of the 28-O-activated compound of example 2 is dissolved in 2 ml DMSO and added dropwise with vigorous stirring to a solution containing 5 mg KLH in 1 ml 50 mM phosphate buffer (PH 7.3). The reaction mixture is stirred for 2 hours at room temperature, and the resulting conjugate is purified by dialysis at 4° C. against 2 l PBS, 3× over 48 hours. Conjugates with BSA and OVA conjugates are prepared in the same manner. Rapamycin is conjugated to KLH, BSA, and OVA through position 28 using the 28-O activated compound of example 3, following the same procedure.

EXAMPLE 5

Production of Monoclonal Antibody
a) Monoclonal Antibody to Rapamycin

Monoclonal antibody is produced by using conventional techniques, essentially as described by Köhler and Milstein in Nature 256: 49. Female Balb/C mice (20–25 g) each receive 10 or 50 μg of the 40-O-linked rapamycin-KLH immunogenic conjugate of example 4a) in 0.2 ml complete Freund adjuvant, administered by subcutaneous injection at four sites. After 2 weeks a second booster injection comprising the same amount of the immunogenic conjugate emulsified in 0.2 ml of incomplete Freund adjuvant is administered, again by s.c. injection. The presence of antibodies reactive to the antigen in the animals' blood serum is confirmed by direct ELISA as described in example 6 below. The mice may optionally be further selected for antibody to the effector region (low cross reactivity with FK-506) and to the FKBP binding region (high cross reactivity to FK-506). FIG. 1, for example, shows titer curves for a mouse (M1) having a high level of antibody to the binding domain of rapamycin, and another mouse (M7) having relatively high levels of antibody to the effector domain. Mice displaying maximal blood serum levels of antibody of appropriate specificity receive booster injections comprising 10 μg of antigen half i.p. half i.v. on day −3, and i.p. on day −2 and −1. On day 0. the mice are sacrificed and their spleen cells are isolated and fused with PAI-0 cells or other suitable myeloma line. The resulting hybridomae are cultured and selected using ELISA for expression of antibody having a high affinity to rapamycin.

b) Monoclonal Antibody to 40-(hydroxyethyl)-rapamycin

Female Balb/C mice receive 10 or 50 μg of the 40-(hydroxyethyl)-rapamycin KLH immunogenic conjugate of example 4b) in 0.2 ml complete Freund's adjuvant by s.c. injections on 4 points. After 2 weeks, a second injection (booster) comprising the same quantity of immunogenic conjugate emulsified in 0.2 ml incomplete Freund's adjuvant is administered, again by s.c. injection. The presence of antibodies reactive to the antigen in the animal's blood serum is tested by direct ELISA as described below. In addition, mice are further selected for antibody to the region of the rapamycin molecule modified in the 40-O region by binding to a conjugate of BSA-rapamycin compared to a conjugate of BSA-40-O(2-hydroxyethyl)-rapamycin. Both antibodies which bind to the 40-O(2-hydroxyethyl)-rapamycin conjugate but do not bind to conjugated rapamycin, and antibodies which bind both to 40-O(2-hydroxyethyl)-rapamycin and rapamycin conjugates are obtained. Mice displaying maximal blood serum levels of antibody of appropriate specificity receive booster injections comprising 10 μg of antigen half i.p. half i.v. on day −3, and i.p. on day −2 and −1. On day 0. the mice are sacrificed and their spleen cells are isolated and fused with PAI-0 cells. The resulting hybridoma are cultured and selected using ELISA for expression of antibody having a high affinity to 40-O-(2-hydroxyethyl)-rapamycin.

EXAMPLE 6

Enzyme Linked Immunosorbent Assay (ELISA)
a) ELISA for Rapamycin

Microtiter plates are coated with 1–2 μg/ml rapamycin-BSA conjugate in PBS for 2 hours at 37° C., then saturated with 2% BSA in PBS for 1 hour at 37° C., and washed 3× with 0.05% Tween-PBS. The hybridoma supernatants to be screened are diluted in a 1% solution of BSA in PBS, and incubated overnight at room temperature (or 18 hours at 4° C. or 2 hours at 37° C.). Level of bound antibody is measured by anti-mouse IgG goat globulin coupled to alkaline phosphatase with para-nitrophenylphosphate as the substrate. After incubation for two hours at 37° C., the enzymatic substrate is hydrolysed (i hour at room temperature) and absorbance at 405 nm is measured. Hybridomae are selected for production of high affinity monoclonal antibody.

Figure 2:
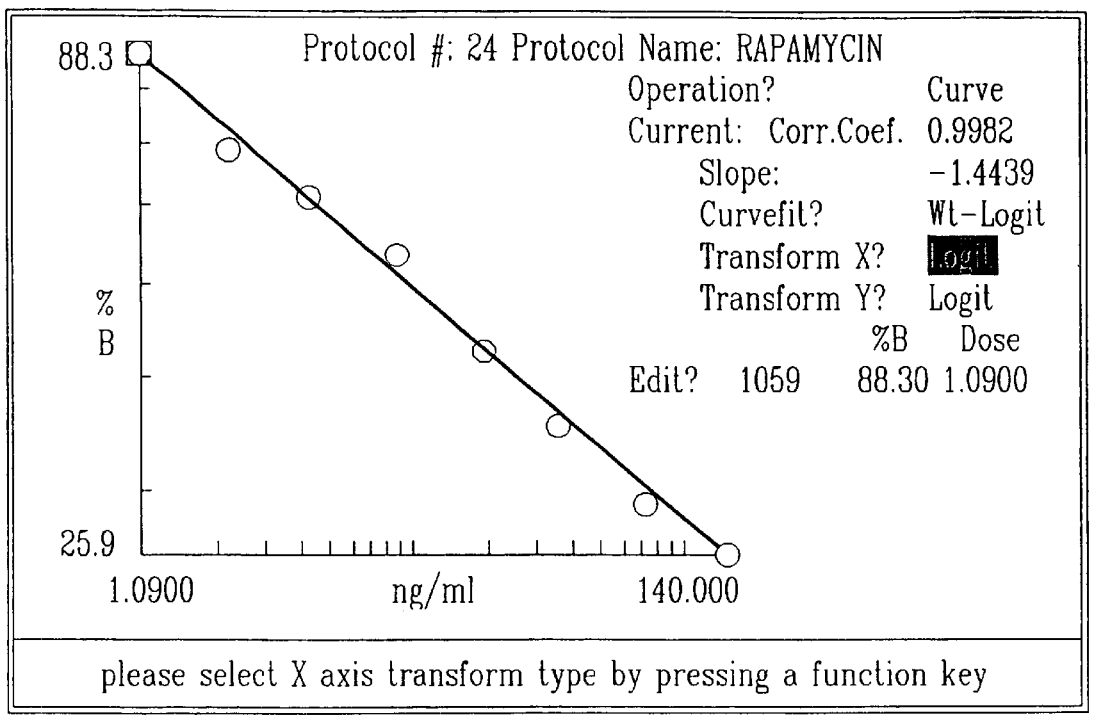

Standard curves to determine relative affinity of a selected antibody to rapamycin are prepared using solutions containing known concentrations of rapamycin (e.g., 1 to 140 ng/ml in blood serum). FIG. 2, for example, shows a standard curve for our monoclonal antibody M7-91, demonstrating that that monoclonal antibody, which was selected as being highly specific for rapamycin, is capable of detecting rapamycin at levels as low as 0.25 ng/ml.

Figure 3:
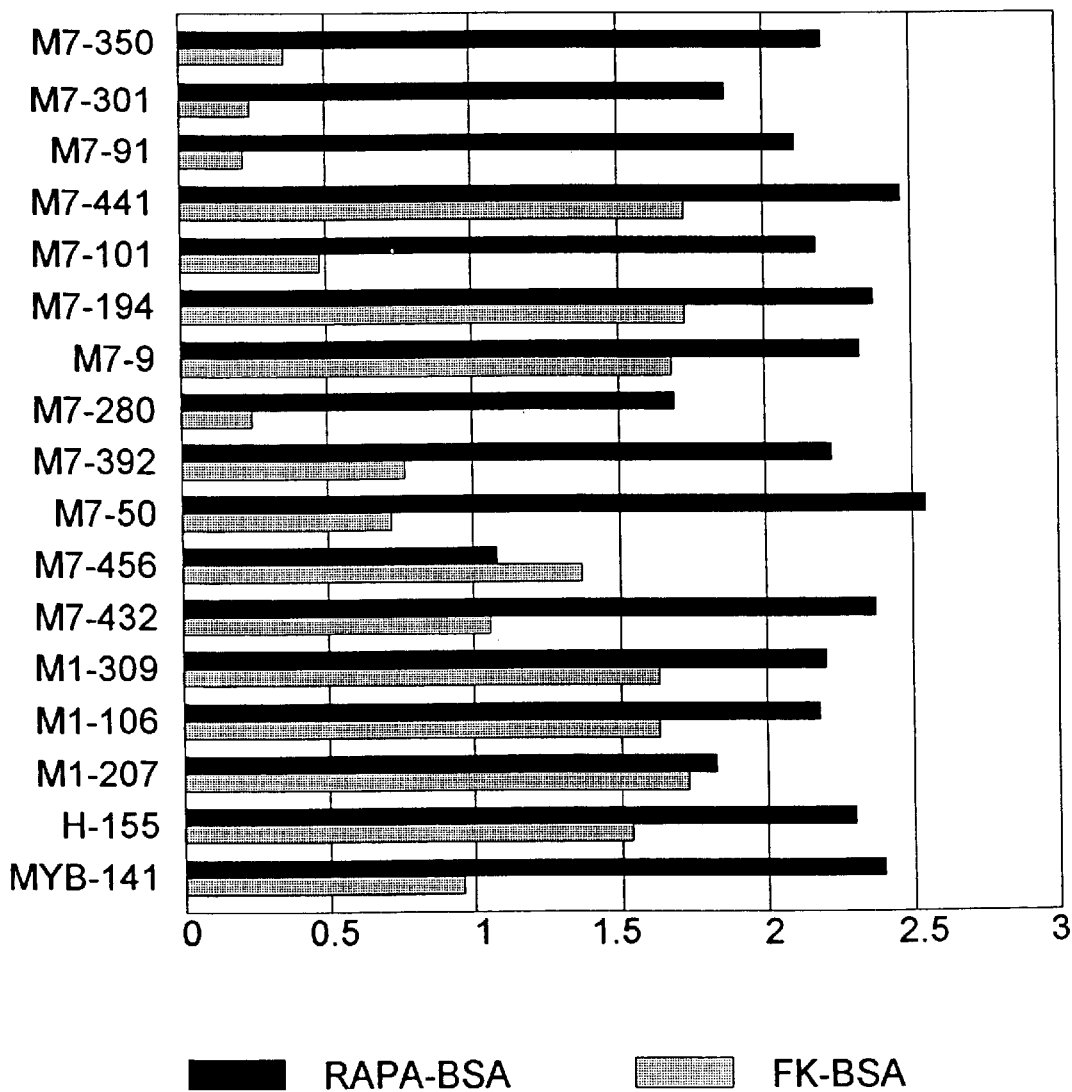
Figure 4:
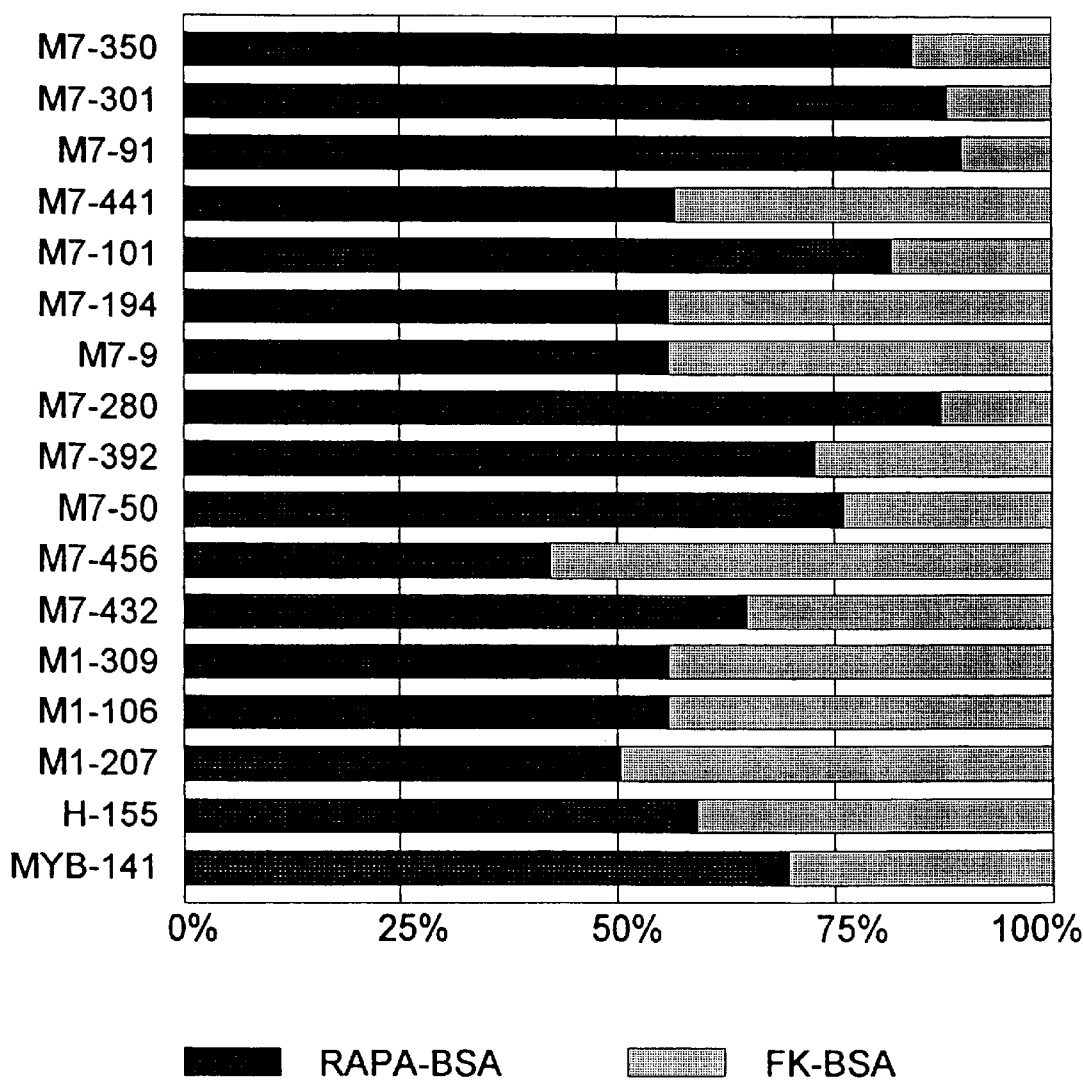

Antibodies may be further characterized as binding to the effector or FKBP binding domains of rapamycin by measuring cross reactivity with FK-506 in an analogous direct ELISA using microtiter plates coated with FK506-BSA conjugate, which can be prepared analogously to rapamycin-BSA conjugate. For example, a comparison of binding levels of 17 selected monoclonal antibodies in the rapamycin-BSA and FK-506 assays is shown in FIG. 3; cross reactivity as a percentage is shown in FIG. 4. In this comparison of binding to rapamycin-BSA vs. FK506-BSA, monoclonal antibodies of very low affinity are detected.

Figure 5:
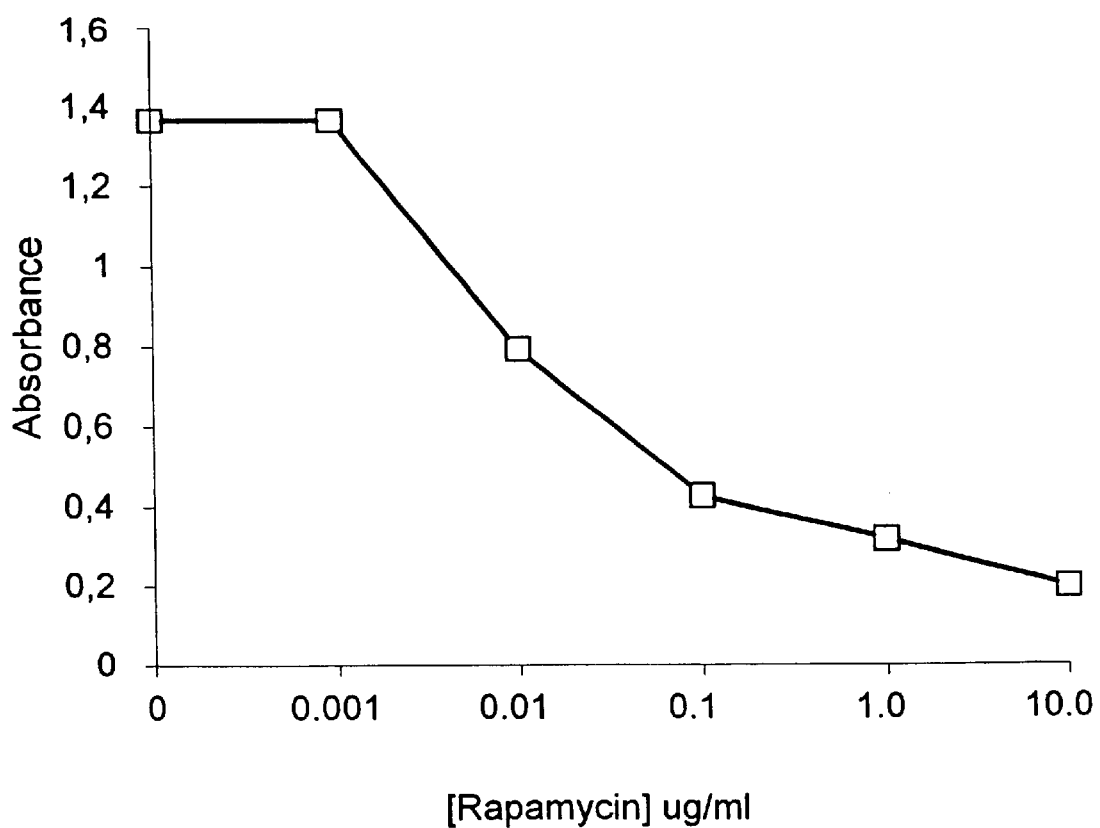
Figure 6:
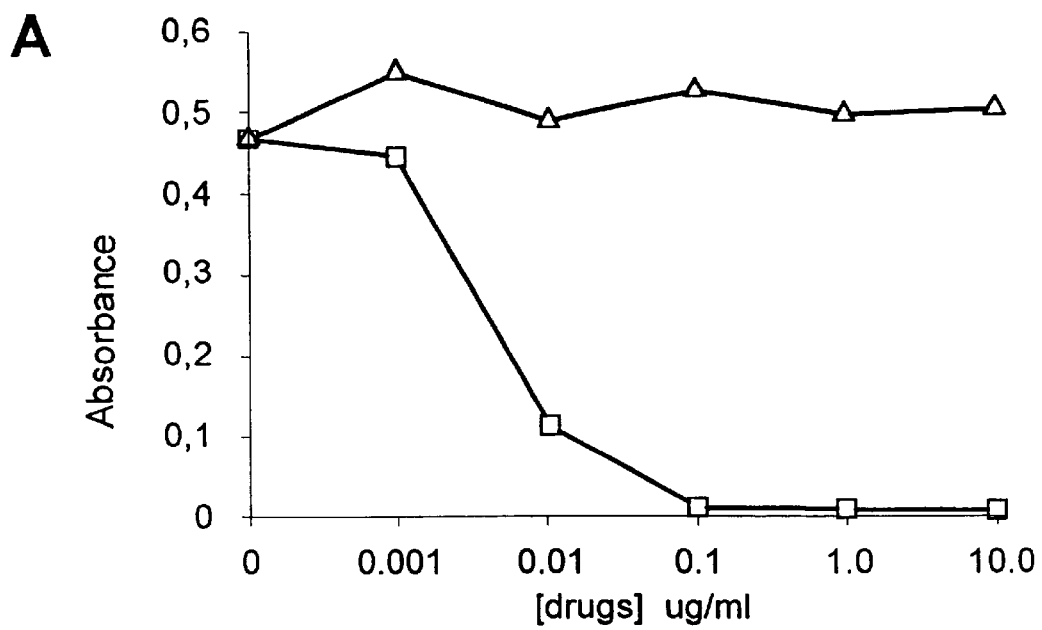
Figure 6:
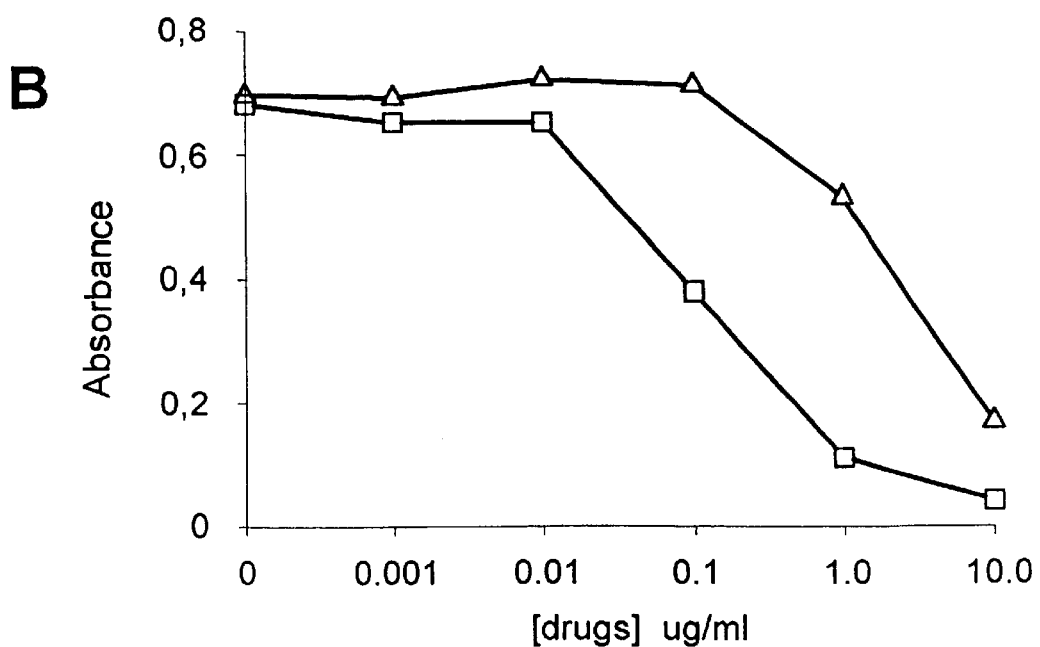

The above direct ELISA may be converted to a competitive ELISA wherein a competitor is added to the monoclonal antibody solution, and binding of the monoclonal antibody to the conjugate in the presence and absence of the competitor is measured. Where the competitor is FK506 or a rapamycin, the competitor in ethanolic solution, e.g., 1 mg/ml is directly added to the monoclonal antibody solution (e.g., 2 μl/200 μl/well) and further diluted in the microtiter plate. FIG. 5, for example, shows an inhibition curve for binding of the M7-91 antibody (M7.91.13) to BSA-rapamycin in the presence of different concentrations of free rapamycin. In such competitive ELISAs comparing the binding of the monoclonal antibodies to free FK506 vs. free rapamycin, less cross reactivity between rapamycin and FK506 is seen than in the direct ELISA. Such a competitive assay is preferred for selection of monoclonal antibodies, because it is believed that some monoclonal antibodies may have too low an affinity to bind their antigen in free form in solution but may nevertheless show bivalent or polyvalent binding to the multimeric antigen, which comprises many haptens bound in close proximity to one another on a large protein molecule. A competitive assay excludes such low affinity antibodies. The results of such a competitive assay are shown in FIG. 6, which compares the M7-91 antibody (M7.91.13) which has relatively low cross reactivity with M1-303 (M1.303.3) antibody which has relatively high cross reactivity.

b) ELISA for 40-O-(2-hydroxyethyl)-rapamycin

Figure 7:
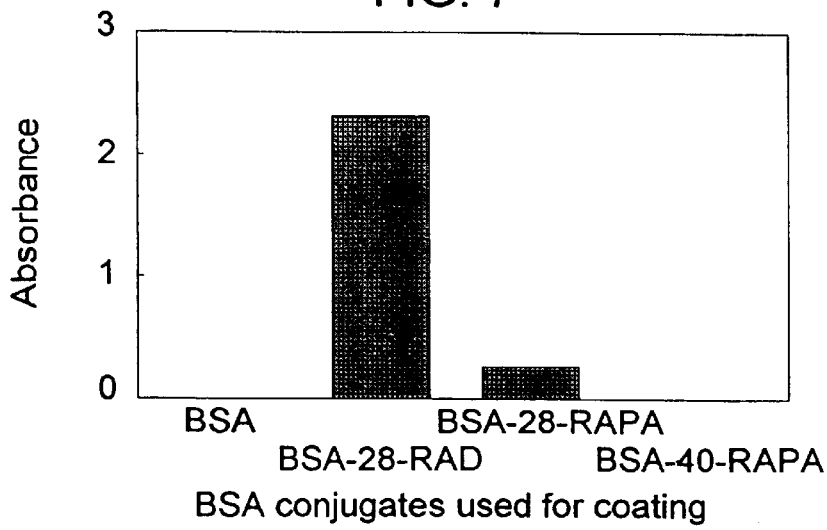
Figure 7:
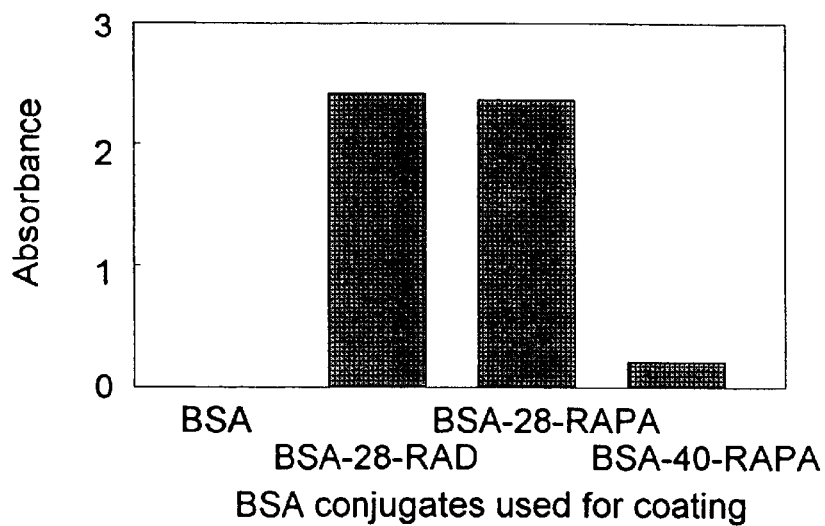
Figure 7:
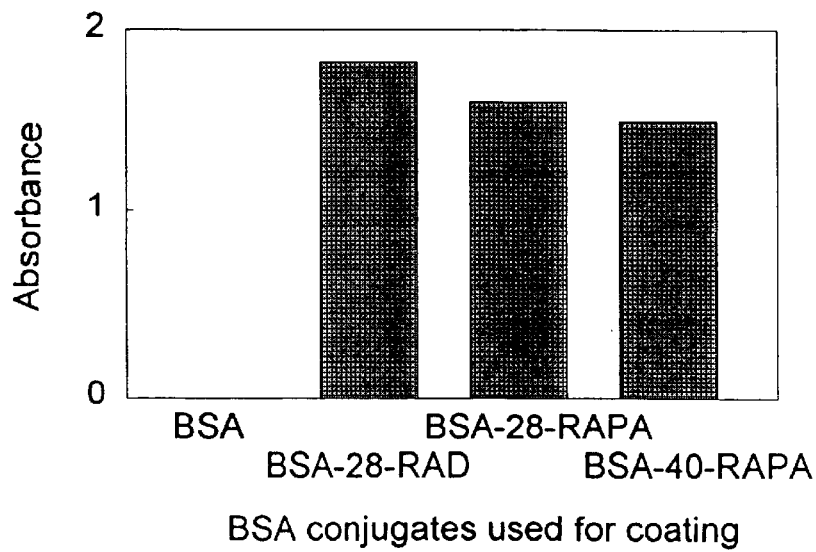

This ELISA is performed analogously to the procedure described in a). Microtiter plates are coated with 40-O-(2-hydroxyethyl)-rapamycin-BSA, saturated with BSA and washed. The hybridoma supernatants to be screened are incubated 18 hours at 4° C. or 2 hours at 37° C. Level of bound antibody is measured by anti-mouse IgG goat globulin coupled to alkaline phosphatase with para-nitrophenylphosphate as the substrate. A parallel ELISA is performed using bound rapamycin-BSA to select for monoclonal antibodies capable of distinguishing 40-O-(2-hydroxyethyl)-rapamycin from rapamycin. FIG. 7 shows, for example, supernatants of hybridoma B3-203 binding selectively to 40-O-(2-hydroxyethyl)-rapamycin-BSA (referred to in the figure as BSA-28-RAD) (FIG. 7A), of hybridoma B3-113 recognizing both 40-O-(2-hydroxyethyl)-rapamycin-BSA and rapamycin-BSA conjugated through position 28 (FIG. 7B), and of hybridoma B3-164 that recognize in addition rapamycin coupled to BSA through position 40 (FIG. 7C).

Figure 8:
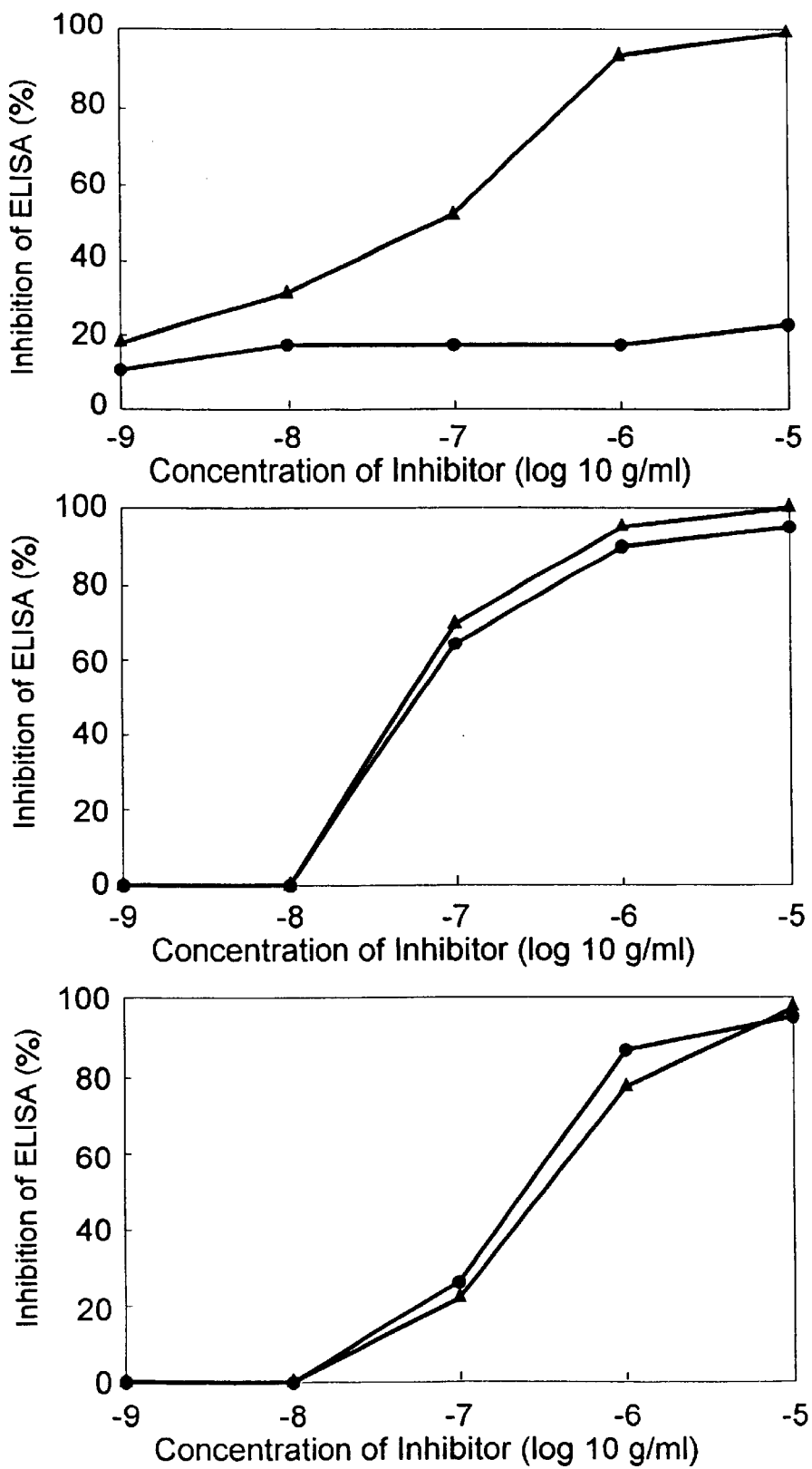

The relative affinity of the antibodies to 40-O-(2-hydroxyethyl)-rapamycin versus rapamycin is further measured by competing the binding of the antibodies to the coated 40-O-(2-hydroxyethyl)-rapamycin-BSA conjugate with 40-O-(2-hydroxyethyl)-rapamycin or rapamycin free in solution. FIG. 8, for example, shows that antibodies produced by hybridoma B3-203 react strongly with 40-O-(2-hydroxyethyl)-rapamycin with low crossreactivity for rapamycin (FIG. 8A) and that antibodies produced by hybridoma B3-113 and B3-164 bind equally well to 40-O-(2-hydroxyethyl)-rapamycin and rapamycin (FIGS. 8B and 8C). Other hybridomae producing antibodies binding at least 10–100-fold better to 40-O-(2-hydroxyethyl)-rapamycin than to rapamycin include B3-22, B3-127 and B3-156. Other hybridomae such as B3-29, B3-265 and B3-539 produce antibodies that bind rapamycin as well as 40-O-(2-hydroxyethyl)-rapamycin.

Once the desired antibody has been selected, the same ELISA is used to determine blood levels of rapamycin in patients. An assay kit according to this example would provide one or more selected antibodies in lyophilized form, a microtiter plate coated with a rapamycin conjugate (e.g., rapamycin-BSA conjugate or 40-O-(2-hydroxyethyl)-rapamycin-BSA conjugate), a rapamycin standard, and instructions for use. Optionally, the kit may further comprise a labelled rapamycin derivative for use in a competitive assay. Anti-mouse IgG-enzyme conjugate and substrate as described above may additionally be provided. Alternatively, the customer may use the monoclonal antibody of the invention in his own established ELISA or other assay system.

What is claimed is:

1. An immunogenic conjugate which is 1) rapamycin bearing an immunogenic protein at position 40 or 28; or 2) 40-O-(2-hydroxyethyl)-rapamycin bearing an immunogenic protein at position 28.

2. An immunogenic conjugate of claim 1 which is produced by reacting an immunogenic protein with either 1) rapamycin bearing an activated coupling group at position 40 or 28; or 2) 40-O-(2-hydroxyethyl)-rapamycin bearing an activated coupling group at position 28, wherein the activated coupling group is —CO—O—X where X is a carboxy activating group, —S—S—Z where Z is a dithio activating group, or an epoxy group.

3. An immunogenic conjugate comprising a rapamycin portion and a protein portion wherein the rapamycin is i) 40-O-succinimidooxysuccinyl-rapamycin, ii) 28-O-succinimidooxysuccinyl-rapamycin, or iii) 28-O-(succinimidooxysuccinyl)-40-O-(2-hydroxyethyl)-rapamycin.

4. An immunogenic conjugate which is produced by reacting a protein with a rapamycin derivative bearing an activated coupling group wherein the rapamycin is i) 40-O-succinimidooxysuccinyl-rapamycin, ii) 28-O-succinimidooxysuccinyl-rapamycin, or iii) 28-O-(succinimidooxysuccinyl)-40-O-(2-hydroxyethyl)-rapamycin.

* * * * *

UNITED STATES PATENT AND TRADEMARK OFFICE
CERTIFICATE OF CORRECTION

PATENT NO. : 6,635,745 B2  Page 1 of 1
DATED : October 21, 2003
INVENTOR(S) : Sedrani et al.

It is certified that error appears in the above-identified patent and that said Letters Patent is hereby corrected as shown below:

<u>Title page,</u>
Item [63], Related U.S. Application Data, should read:
-- [63] This is a continuation of Application 09/072,278, May 4, 1998, abandoned, which is a continuation of Application 08/532,837, October 5, 1995, abandoned, which is a 371 of PCT/EP94/01006, March 30, 1994. --

Signed and Sealed this

Tenth Day of February, 2004

JON W. DUDAS
*Acting Director of the United States Patent and Trademark Office*

Adverse Decision in Interference

Patent No. 6,635,745, Richard Sedrani, Valerie Quesniaux Ryffel, RAPAMYCIN ASSAY, Interference No. 105,429, final judgment adverse to the patentees rendered February 6, 2007, as to claims 1-4.
(*Official Gazette* June 12, 2007)